United States Patent [19]

Greth

[11] Patent Number: 4,540,808

[45] Date of Patent: Sep. 10, 1985

[54] PROCESS FOR THE PREPARATION OF 4-ALKOXYACETOACETIC ACID ESTER

[75] Inventor: Erich Greth, Visp, Switzerland

[73] Assignee: Lonza, Ltd., Gampel, Switzerland

[21] Appl. No.: 423,568

[22] Filed: Sep. 27, 1982

[30] Foreign Application Priority Data

Oct. 1, 1982 [CH] Switzerland ............... 6321/81

[51] Int. Cl.$^3$ .................................................. C07 69/72
[52] U.S. Cl. ...................................... 560/178; 560/53
[58] Field of Search .................................. 560/178, 13

[56] References Cited

FOREIGN PATENT DOCUMENTS 562191 4/1975 Switzerland ........................ 560/178

OTHER PUBLICATIONS

Bull. Soc. Chim., France, 4th Series, 29 (1921), pp. 402–406.

Primary Examiner—Paul J. Killos
Attorney, Agent, or Firm—Fisher, Christen & Sabol

[57] ABSTRACT

Process for the production of 4-alkoxyacetoacetic acid esters from 4-chloro- or 4-bromoacetoacetic esters. The 4-chloro- or 4-bromoacetoacetic ester is reacted with a highly concentrated solution of an alkali alcoholate in alcohol having been concentrated at elevated temperatures, at temperatures of 50° to 120° C. At least 2.8 mole of the alkali alcoholate are used per mole of 4-chloro- or 4-bromoacetoacetic ester.

11 Claims, No Drawings

PROCESS FOR THE PREPARATION OF 4-ALKOXYACETOACETIC ACID ESTER

BACKGROUND OF THIS INVENTION

1. Field Of This Invention

This invention relates to a process for the production of 4-alkoxyacetoacetic esters.

2. Prior Art 4-ethoxyacetoacetic ester has been produced by reaction of bromoacetic ester and ethoxyacetic ester with zinc [J. Amer. Chem. Soc., 68, (1946), 2392] or by reaction of ethoxyacetic ester with acetic ester in the presence of sodium [Chem. Abstr., 43, (1949), 2625e]. 4-methoxyacetoacetic ester has been produced by condensation of methoxyacetylchloride with malonic acid ethyl tert.-butyl ester with subsequent saponification and decarboxylation [J. Amer. Chem. Soc., 70, (1948), p. 500]. The yields obtained according to these processes are in the neighborhood of 11, 21 or 40 percent, respectively.

Experiments designed to produce 4-ethoxyacetoacetic ester from 4-chloroacetoacetic ester with equimolar quantities of Na-alcoholates in alcohol failed. Instead of the anticipated 4-ethoxyacetoacetic ester diethyl, succinyl succinate was obtained [Bull. Soc. Chim. France, 4th series, 29, (1921), pp. 402–406].

Swiss Pat. No. 562,191 teaches the successful production of 4-alkoxyacetoacetic esters from 4-haloacetic esters with alkali alcoholates whenever the operation is conducted in a mixture of an alcohol and an aprotic solvent with high dielectricity constant, preferably dimethyl sulfoxide, at a temperature of 15° to 30° C. The disadvantages of such process are that reaction times of 24 to 72 hours are required and that the reaction must be carried out in a large quantity of the solvent mixture.

T. Kato, J. Chem. Soc., Perkin I, 529, (1979), teaches the production of 4-ethoxyacetoacetic ester from 4-bromoacetoacetic ester. At the same time, one equivalent of 4-bromoacetoacetic ester is reacted with 2.2 equivalents of sodium ethylate. Large quantities of ethanol serve as the solvent, but the yields of 47 percent are very modest.

BROAD DESCRIPTION OF THIS INVENTION

An object of this invention is to provide a process for the production of the hitherto difficultly accessible 4-alkoxyacetoacetic ester in high yields with a simple execution and a short reaction time. Another object of this invention is to provide a composition for use in said process. Other objects and advantages of this invention are set out herein or are obvious herefrom to one ordinarily skilled in the art.

The objects and advantages of this invention are achieved by the process and composition of this invention.

This invention involves a process for producing 4-alkoxyacetoacetic acid esters, which can be substituted in the 2-position with a substituent which does not react in a strongly basic medium. The process includes the reaction of 4-chloroacetoacetic ester or 4-bromoacetoacetic ester with a highly-concentrated solution of alkali alcoholate in an alcohol having been concentrated at an elevated temperature. At least 7 mole of an alcohol are used per moles of 4-haloacetoacetic ester and are reacted at an elevated temperature. The alkali alcoholate is used in a concentration of 10 percent up to about 40 percent by weight, and preferably 20 to 35 percent by weight. This data means percent by weight in the solution at the beginning of the reaction.

In case of the low alcohols (methanol or ethanol), real solutions are involved; in the case of the higher alcohols, the solutions still containing undissolved alcoholate (suspension) can be used. The range of concentration of the alkali alcoholate is limited on the lower end by the decreasing yield and on the upper end essentially by the stirrability of the reaction mixture. In the course of the reaction of the invention alkali halide develops which is obtained as a solid substance; if the reaction mixture is too concentrated, the suspended alkali halide leads to non-stirrable reaction mixtures. Such concentrated alcoholate solutions can be obtained by charging a vessel with the corresponding alkali metal adding, the alcohol slowly by doses and finally heating the mixture to a temperature of 50° to 120° C. until all of the metal is dissolved. Such concentrated alcoholate solutions, however, can also be produced by dissolving or suspending solid alkali alcoholate in the corresponding alcohol.

The temperature for dissolving the alkali metal or alkali alcoholate is about 50° to 120° C. At temperatures, lower than 50° C. concentrations being sufficient for the reaction are not acheived; in the case of a higher temperature, there is the danger of decompositon. When using methanol or ethanol, preferably operation occurs at reflex temperature.

The 4-haloacetoacetic ester is added in doses into the saturated alkali alcoholate solution.

As a reaction temperature, preferably the same temperature is selected at which the production of the alkali alcoholate solution has been undertaken, however, this is not absolutely necessary. On the lower end, the reaction temperature is limited by increasing reaction times as well as the decreasing solubility of the alkali alcoholates; on the upper end, possible decomposition of educts or products are a factor. In the case of reactions in methanol or ethanol, the reflux temperature is optimal.

The reaction time effectively is 15 minutes to several hours (depending on the reaction temperature), and preferably is 30 minutes to 1 hour.

The alkali alcoholate is used advantageously in a quantity of more than 2.8 mole, preferably 3 to 4 mole, per mole of 4-haloacetoacetic ester. The alkali metal in the alkali alcoholates are effectively sodium and potassium. The alcohol component of the alkali alcoholate are those which are derived from straight-chained or branched aliphatic alcohols, effectively those which have 1 to 4 carbon atoms in the molecule. Such alcohols are, for example, methanol, ethanol, butanol, sec. butanol, propanol and isopropanol.

Of the 4-chloroacetoacetic esters or 4-bromoacetoacetic esters, especially the 4-chloro derivatives are used. 4-chloroacetoacetic esters and 4-bromoacetoacetic esters substituted in the 2-position can also be used. Thus, the process of this invention produces a 4-alkoxyacetoacetic ester having the general formula:

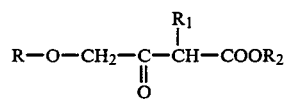

wherein R and $R_2$ are each alkyl and $R_1$ is H or alkyl. The substituents R, $R_1$ and $R_2$ are subject to no numerical limitation of the included C atoms, but usually 1 to 12 carbon atoms are present. Any alkyl groups, whether straight-chained or branched, can be used. Substituted alkyl groups, for example, with methoxy, alkyl and/or aryl groups, can be used. An essential characteristic of such substituents is that they do not react in a strongly basic medium. Examples of useful alkyl groups are methyl, ethyl, propyl, isopropyl, n-butyl, isobutyl, 2-butyl, 1 -pentyl, 3-methyl-1-butyl, 2-pentyl, 1-hexyl, 2-methyl-1-pentyl, 3-methyl-1-pentyl, 4-methyl-1-pentyl, 2-ethyl-1-butyl, 2-hexyl, 2,3-dimethyl-1-butyl, 1-heptyl, 2,4-dimethyl-1-pentyl, 1-octyl, 2-octyl, 1-nonyl, 1-decyl, 1-undecyl, 1-dodecyl, 1-tetradecyl and 1-nonadecyl.

The process of this invention is particularly suited for the production of 4-alkoxyacetoacetic esters in which the 4-alkoxy group and the alcohol group of the ester are identical. When this process is used in the production of 4-alkoxyacetoacetic esters, in which the 4-alkoxy group is different from the alcohol group of the ester, then ester mixtures are obtained upon trans-esterification.

The 4-alkoxyacetoacetic ester is obtained from the reaction mixture available after the reaction, preferably in accordance with the following method:

While stirring, a mineral acid (hydrochloric acid gas, sulfuric acid) is added in doses to the reaction mixture in such a way that at the end of such addition a pH value of 5 to 7 (neutralization) is achieved. The neutralized reaction solution can be processed further in various ways into the desired 4-alkoxyacetoacetic ester. For example, the reaction solution can be freed of alcohol in a rotary evaporator, effectively at 20 torr vacuum, with the residue being absorbed in water. This aqueous phase is extracted with a solvent, for example, ethylacetate, and the solvent distilled off.

By way of summary, this invention involves a process for preparing 4-alkoxyacetoacetic esters from 4-haloacetoacetic esters and alkali alcoholate. A saturated solution of an alkali alcoholate in an alcohol is used.

DETAILED DESCRIPTION OF THIS INVENTION

As used herein, all parts, ratios, percentages and proportions are on a weight basis unless otherwise stated herein or otherwise obvious herefrom to one ordinarily skilled in the art.

EXAMPLE 1

A sulfurizing flask was flushed with initrogen and charged with 90 g of sodium. 530 g of methanol was added drop by drop. After completion of the addition, the contents were heated in an oil bath up to reflux. The heating (with stirring ) was continued until all of the sodium was dissolved (3 to 4 hours). Then the oil bath was removed and 201.30 g of 4-chloroacetoacetic methyl ester was allowed to run into the flask while vigorously stirring the contents (about 6 minutes). After completion of the addition, the oil bath was again brought back and used to boil the flask contents for 30 minutes at the reflux. The flask contents were neutralized at the boiling temperature with hydrochloric acid gas to a pH of 6.65, using the help of a pH meter and a combined glass electrode. This reaction solution was freed from methanol using rotary evaporator at 20 torr of terminal vacuum and 60° to 70° C. of bath temperature. The residue was absorbed in 650 ml of water and was extracted five times with acetic ester (once with 200 ml, and four times with 100 ml). The acetic ester was distilled off by means of a short distillation column. 203.70 g of raw product was obtained. The crude ester was distilled at 80° C./8 torr by means of a 60 cm Vigreux column having a vacuum jacket. 158.49 g of distilled 4-methoxyacetoacetic methyl ester was obtained as a colorless fluid - this corresponded to a yield of 80.57 percent. The purity was about 97.8 percent.

EXAMPLES 2 AND 3

Using the procedure of Example 1, additional experiments were carried out. As starting compound, 4-chloroacetoacetic acid octyl ester was used in both cases and, as the alcoholate, sodium ethylate was used once and sodium octanoate was used the other time. The yield achieved in Example 2 was 80.8 percent, and in Example 3 was 79.2 percent, based on the amount of 4-chloro ester used.

EXAMPLE 4

This is a comparative example; it is not within this invention. 15.56 g of 4 -chloroacetoacetic acid methyl ester (0.105 mole) was allowed to react in 200 ml of methanol with 5.51 sodium (0.240 mole, i.e., 2.28 mole per mole of 4-chloroacetoacetic methyl ester) at 20° C. over a 48 hour period. A black oil was isolated which contained 5.31 g of 4-methxoyacetoacetic ester corresponding to a 35.2 percent yield, based on the amount of 4-chloroacetoacetic methyl ester used. Beside that product, 6.15 g of non-volatile by-products (resin) was obtained. 1.16 part of resin was formed per 1 part of product.

EXAMPLE 5

This is a comparative example; it is not within the scope of this invention.

7.24 g of 4-chloroacetoacetic methyl ester (0.049 mole) was reacted with a solution of 5.75 sodium (0.25 mole, i.e., 5.1 mole per mole of 4-chloroacetoacetic methyl ester) in 200 ml of methanol for 1 hour at reflux temperature. The reaction product contained 3.62 g of 4-methyoxyacetoacetic methyl ester, corresponding to a 51.7 percent yield (based on the amount of 4-chloroacetoacetic ester used), as well as 2.63 g of non-volatile resin. 0.73 part of non-volatile by-product was obtained per 1 part of product.

EXAMPLE 6

14.75 g of 4-chloroacetoacetic methyl ester (0.10 mole) in a solution of 23.06 g of sodium (1 mole, 10 times excess) in 200 ml of methanol was refluxed for 1 hour. 13.26 g of 4-methyoxyacetoacetic methyl ester was found in the reaction product corresponding to a 92.7 percent yield. 0.44 g of non-volatile by-products (resins) was also found. For 1 part of product, only 0.033 part of resin was obtained.

EXAMPLE 7

30.70 of 4-chloroacetoacetic methyl ester (0.208 mole) in a solution of 22.95 g of sodium (0.999 mole, 4.8 times excess) in 200 ml of methanol was refluxed for 1 hour. In the reaction product, 25.97 g of 4-methoxyacetoacetic methyl ester was found, which corresponded to 87.2 percent of yield, based on the amount of 4-chloroacetoacetic methyl ester used. Beside that, 1.76 g of resin was obtained. 0.068 part of resin was obtained per 1 part of products.

EXAMPLE 8

Using the procedure of Example 1, 69.0 g of metallic sodium was dissolved in 500 ml of ethanol at reflux temperature. 151.63 g of 4-chloroacetoacetic acid ethyl ester was allowed to run into the solution; the addition lasted 15 minutes. During the addition, the admixture was kept at reflux temperature. After completion of the addition, the admixture was refluxed for another 15 minutes. Then the admixture was neutralized with concentrated sulfuric acid to a pH value of about 6, and was processed as in Example 1. 162.47 g of crude 4-ethoxyacetoacetic ester was obtained. Distillation produced 147.05 g of 4-ethoxyacetoacetic ester having a content of 96.8 percent (gas chromatography), which corresponded to 142.35 g of 100 percent product, and corresponded to a 88.7 percent of yield, based on the amount of 4 -chloroacetoacetic ethyl ester used. 9.80 g of nonvolatile residue remained as distillation residue, that is 0.069 part of residue per 1 part of 4-ethoxyacetoacetic acid ethyl ester, 100 percent.

What is claimed is:

1. Process for the production of a 4-alkoxyacetoacetic acid ester from a 4-chloroacetoacetic ester or 4-bromoacetoacetic ester consisting of reacting a 4-chloroacetoacetic ester or 4-bromoacetoacetic ester with a highly concentrated solution of alkali alcoholate in an aliphatic alcohol having been concentrated at a temperature of 50° to 120° C., at least 2.8 mole of alkali alcoholate being present per mole of 4-chloroacetoacetic ester or 4-bromoacetoacetic ester, at least 7 moles of the alcohol being present per mole of the 4-chloroacetoacetic ester or 4-bromoacetoacetic ester, and 10 to about 40 weight percent of the alkali alcoholate being present based on the starting solution of the reactants, whereby the 4-alkoxyacetoacetic acid ester results, the 4-alkoxyacetoacetic acid ester has the formula:

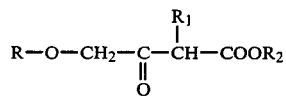

wherein R and $R_2$ are each alkyl, and $R_1$ is H, alkyl or substituted alkyl.

2. Process as claimed in claim 1 wherein 3 to 4 mole of alkali alcoholate are used per mole of 4-chloroacetoacetic ester or 4-bromoacetoacetic ester.

3. Process as claimed in claim 1 wherein $R_1$ is alkyl substitued with methoxy or aryl.

4. Process as claimed in claim 1 wherein the alcohol is ethanol or methanol.

5. Process as claimed in claim 1 wherein 3 to 4 moles of the alkali alcoholate are used per mole of the 4-chloroacetoacetic ester or 4-bromoacetoacetic ester.

6. Process as claimed in claim 1 wherein $R_1$ is an alkyl group, having 1 to 12 carbon atoms, substituted with methoxy or aryl.

7. Process as claimed in claim 1 wherein the reaction is carried out over a time period of 15 minutes to one hour.

8. Process as claimed in claim 1 wherein R is an alkyl group having 1 to 12 carbon atoms, $R_1$ is an alkyl group having 1 to 12 carbon atoms and $R_3$ is an alkyl group having 1 to 12 carbon atoms.

9. Process as claimed in claim 1 wherein the alkali metal in the alkali alcoholate is sodium or potassium and the alcohol component of the alkali alcoholate is an aliphatic alcohol having 1 to 4 carbon atoms.

10. Process for the production of a 4-alkoxyacetoacetic acid ester from a 4-chloroacetoacetic ester or 4-bromoacetoacetic ester consisting of (a) reacting a 4-chloroacetoacetic ester or 4-bromoacetoacetic ester with a highly concentrated solution of alkali alcoholate in aliphatic alcohol having been concentrated at an elevated temperature, at a temperature of 50° to 120° C., at least 2.8 mole of alkali alcoholate being present per mole of 4-chloroacetoacetic ester or 4-bromoacetoacetic ester, at least 7 moles of the alcohol being present per mole of the 4-chloroacetoacetic ester or 4-bromoacetoacetic ester, and 10 to about 40 weight percent of the alkali alcoholate being present based on the starting solution of reactants, whereby the 4-alkoxyacetoacetic acid ester results, the 4-alkoxyacetoacetic acid ester has the formula:

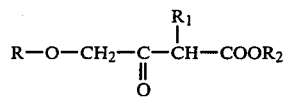

wherein R and $R_2$ are each alkyl, and $R_1$ is H, alkyl or substituted alkyl, and (b) separating the 4-alkoxyacetoacetic acid ester from reaction mixture (a).

11. Process as claimed in claim 10 wherein separation (b) comprises: (i) adding a mineral acid to reaction mixture (a), sufficient mineral acid being added to achieve a pH of 5 to 7 in solution (i); (ii) removing the alcohol from the neutralized solution (i) using an evaporator; (iii) absorbing the residue from step (ii) in water; (iv) extracting aqueous material (iii) with a solvent; and (v) distilling off the solvent from extractant (iv).

* * * * *

UNITED STATES PATENT OFFICE
CERTIFICATE OF CORRECTION

Patent No. 4,540,808    Dated September 10, 1985

Inventor(s) Erich Greth

It is certified that error appears in the above-identified patent and that said Letters Patent are hereby corrected as shown below:

On the face of the patent the line
  [30]    Foreign Application Priority Data  should read as follows:

October 1, 1981  [CH]  Switzerland ....... 6321/81

Signed and Sealed this

Thirty-first Day of December 1985

[SEAL]

Attest:

DONALD J. QUIGG

Attesting Officer    Commissioner of Patents and Trademarks